United States Patent
Wang et al.

(10) Patent No.: US 10,883,961 B2
(45) Date of Patent: Jan. 5, 2021

(54) DETECTING METHOD FOR BLOOD

(71) Applicant: National Tsing Hua University, Hsinchu (TW)

(72) Inventors: Yu-Lin Wang, Hsinchu (TW); Indu Sarangadharan, Hsinchu (TW); Shin-Li Wang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 14 days.

(21) Appl. No.: 16/182,616

(22) Filed: Nov. 7, 2018

(65) Prior Publication Data

US 2019/0162696 A1 May 30, 2019

(30) Foreign Application Priority Data

Nov. 29, 2017 (TW) .............................. 106141700 A

(51) Int. Cl.
  *G01N 33/543* (2006.01)
  *G01N 27/414* (2006.01)
  *G01N 33/50* (2006.01)
  *G01N 33/49* (2006.01)

(52) U.S. Cl.
  CPC ....... *G01N 27/4145* (2013.01); *G01N 27/414* (2013.01); *G01N 33/49* (2013.01); *G01N 33/5091* (2013.01); *G01N 33/5438* (2013.01)

(58) Field of Classification Search
  None
  See application file for complete search history.

(56) References Cited

U.S. PATENT DOCUMENTS 4,758,524 A * 7/1988 Bundesen .............. C07K 16/18
  435/7.92
5,580,794 A * 12/1996 Allen .................... B01L 3/5023
  422/404

(Continued)

FOREIGN PATENT DOCUMENTS

| CN | 101576523 | 11/2009 |
| JP | 2008286714 | 11/2008 |

(Continued)

OTHER PUBLICATIONS

"Search Report of Europe Counterpart Application", dated May 31, 2019, p. 1-p. 9.

(Continued)

*Primary Examiner* — Melanie Brown
(74) *Attorney, Agent, or Firm* — JCIPRNET

(57) ABSTRACT

A detecting method for blood is provided. The method includes the following steps. A sensing device including a base and at least one response electrode is provided, wherein the response electrode is spaced apart from a gate end of the base. Blood including blood cells and targets is disposed on the response electrode. The blood is separated into a first part and a second part, wherein the first part is in contact with the response electrode, and the blood cell count in the first part is less than that in the second part. A voltage is applied on the response electrode, such that an electric field is generated between the response electrode and the gate end of the base, and a detection current generated from the base is measured to detect a characterize of the targets.

15 Claims, 8 Drawing Sheets

(56) References Cited

U.S. PATENT DOCUMENTS

| | | | |
|---|---|---|---|
| 6,565,738 B1* | 5/2003 | Henning | C12Q 1/52 |
| | | | 204/403.01 |
| 7,378,007 B2 | 5/2008 | Moerman et al. | |
| 8,828,713 B2 | 9/2014 | Ren et al. | |
| 9,061,094 B2 | 6/2015 | Hyde et al. | |
| 10,107,824 B2* | 10/2018 | Wang | G01N 33/6893 |
| 10,605,769 B2* | 3/2020 | Wang | A61B 5/0478 |
| 2007/0202561 A1* | 8/2007 | Rosenstein | C12Q 1/004 |
| | | | 435/14 |
| 2007/0231794 A1* | 10/2007 | Dill | C12Q 1/6825 |
| | | | 435/6.11 |
| 2009/0181381 A1* | 7/2009 | Oldham | C12Q 1/6825 |
| | | | 435/6.11 |
| 2009/0188812 A1* | 7/2009 | Broughall | G01N 33/5438 |
| | | | 205/777.5 |
| 2012/0021402 A1* | 1/2012 | Potter | G01N 27/4145 |
| | | | 435/5 |
| 2013/0056367 A1 | 3/2013 | Martinez et al. | |
| 2015/0241423 A1* | 8/2015 | Dilleen | G01N 33/54333 |
| | | | 435/7.92 |
| 2016/0305900 A1 | 10/2016 | Wang et al. | |
| 2017/0016916 A1 | 1/2017 | Wang et al. | |

FOREIGN PATENT DOCUMENTS

| | | |
|---|---|---|
| JP | 4331181 | 9/2009 |
| TW | 201319563 | 5/2013 |
| TW | I464396 | 12/2014 |
| TW | I481386 | 4/2015 |
| TW | I487904 | 6/2015 |
| WO | 2013082600 | 6/2013 |

OTHER PUBLICATIONS

Sarangadharana; Indu et al, "Risk stratification of heart failure from one drop of blood using hand-held biosensor for BNP detection," Biosensors and Bioelectronics, vol. 107, Jun. 1, 2018, pp. 259-265.

Sarangadharana; Indu et al, "Review—High Field Modulated FET Biosensors for Biomedical Applications," ECS Journal of Solid State Science and Technology, vol. 7 No. 7, Mar. 28, 2018, pp. 3032-3042.

Sarangadharana; Indu et al, "Single Drop Whole Blood Diagnostics: Portable Biomedical Sensor for Cardiac Troponin I Detection," Analytical Chemistry, vol. 90, Issue 4, Feb. 20, 2018, pp. 2867-2874.

* cited by examiner

DETECTING METHOD FOR BLOOD

CROSS-REFERENCE TO RELATED APPLICATION

This application claims the priority benefit of Taiwan application serial no. 106141700, filed on Nov. 29, 2017. The entirety of the above-mentioned patent application is hereby incorporated by reference herein and made a part of this specification.

BACKGROUND OF THE INVENTION

Field of the Invention

The invention relates to a biological sample detecting method, and more particularly, to a blood detecting method.

Description of Related Art

The blood detection is one of the important test items in a health examination. In clinical blood detection, the main treatment process is divided into three major steps, which are respectively blood sample extraction, blood sample pretreatment, and detecting. To reduce interference caused by blood cells, the blood sample is usually pretreated to separate the blood cells and plasma, and then the target in the plasma is tested to obtain an accurate test value.

Current methods for separating blood cells and plasma include, for instance, centrifugation, filtration, and fluid mechanics. However, the centrifugation method has disadvantages such as large size, difficult miniaturization, time consuming, and high cost. The filtering method is time consuming. The fluid mechanics method causes difficult miniaturization and increases process difficulty.

Therefore, how to develop a whole blood detecting method without pretreatment is an important topic for those skilled in the art.

SUMMARY OF THE INVENTION

The invention provides a blood detecting method having the properties of low detection limit and high sensitivity and can adopt human whole blood for detecting and reduce interference to the blood cells.

A blood detecting method of the invention includes the following steps. A sensing device is provided, wherein the sensing device includes a base and at least one response electrode, and the response electrode is spaced apart from the base relative to a gate end of the base. Blood is placed on the response electrode, wherein the blood includes a plurality of blood cells and a plurality of targets. The blood is separated into a first part and a second part, wherein the first part is in contact with the response electrode, and the blood cell count of the first part is less than the blood cell count of the second part. A voltage is applied to the response electrode such that an electric field is generated between the response electrode and the gate end of the base and a detection current generated from the base is measured to measure a property of the target.

In one embodiment of the invention, the electric field is F, and F is 0.1V/cm or more.

In one embodiment of the invention, the method of separating the blood into the first part and the second part may include inverting the sensing device in which the blood is placed to separate the blood into the first part and the second part via gravity.

In one embodiment of the invention, the target is, for instance, a disease biomarker.

In one embodiment of the invention, the disease biomarker is, for instance, a cardiovascular disease biomarker, a cancer biomarker, a renal disease biomarker, or an infectious disease biomarker.

In one embodiment of the invention, the sensing device may further include an acceptor disposed on the surface of the response electrode, wherein the acceptor can be specifically bonded to the target.

In one embodiment of the invention, the sensing device may further comprise multiple types of acceptors disposed on a surface of the response electrode, and each type of acceptors can be specifically bonded to its corresponding type of target.

In one embodiment of the invention, the acceptor is, for instance, an antibody or an aptamer.

In one embodiment of the invention, the response electrode and the gate end of the base are located on the same plane.

In one embodiment of the invention, the response electrode is separately disposed above the gate end of the base.

In one embodiment of the invention, the sensing device is, for instance, a high electron mobility transistor, a silicon-based field-effect transistor, a nanowire field-effect transistor, a carbon nanotube field-effect transistor, a graphene field-effect transistor, or a molybdenum disulfide field-effect transistor.

In one embodiment of the invention, the sensing device may include a plurality of response electrodes, and the plurality of response electrodes are spaced apart from one another.

In one embodiment of the invention, the sensing device may further include a plurality of switch circuits, and each of the response electrodes is connected to the corresponding switch circuit.

In one embodiment of the invention, the plurality of response electrodes are arranged in an array and used against the single gate end.

In one embodiment of the invention, the plurality of response electrodes are arranged radially and used against the single gate end.

Based on the above, the blood detecting method of the invention can directly adopt whole blood for detection and interference to blood cells during detection can be reduced. Moreover, in the blood detecting method of the invention, voltage difference is generated to the response electrode and the gate end spaced apart from each other and a capacitance effect is produced by applying a pulse voltage having an tunable pulse width and height to the response electrode to overcome a shielding effect and to directly detect the target in the blood in high salt concentration. Moreover, the detecting method of the invention has a gain effect, and therefore subtle electrical signal can be detected.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
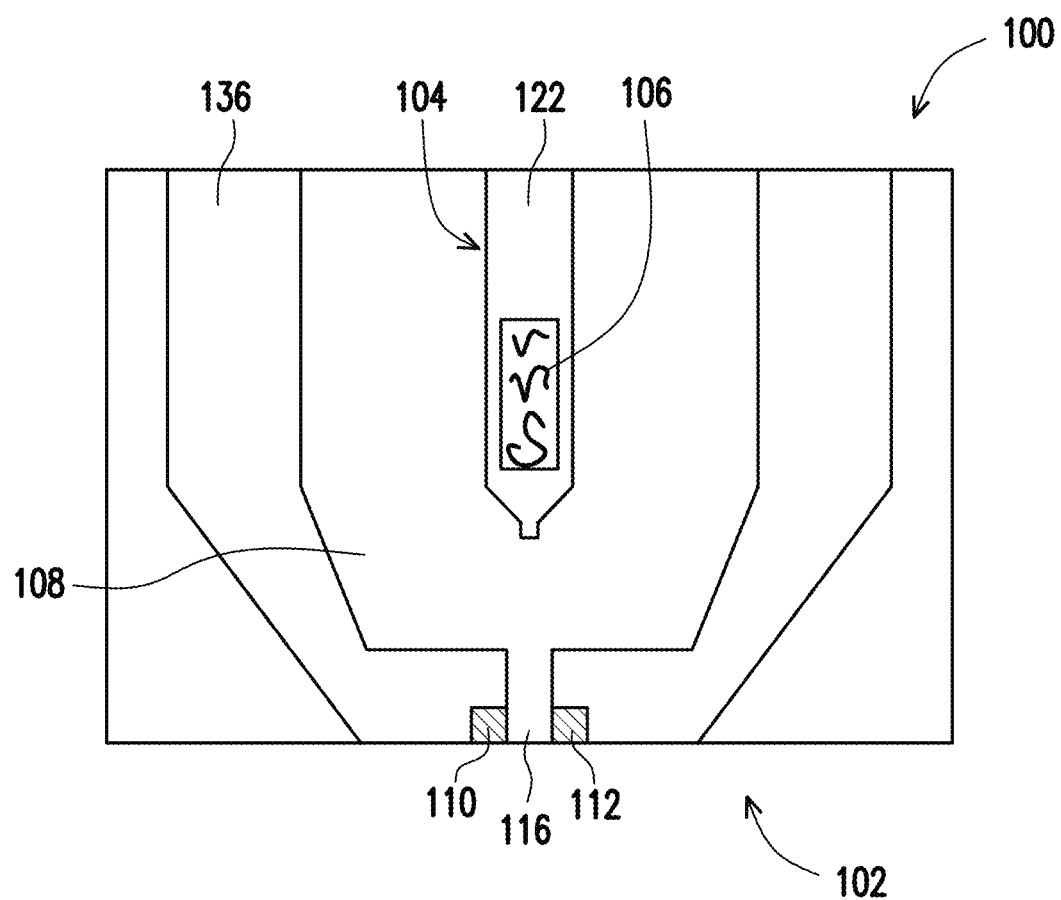
FIG. 1 is a top view of a sensing device according to an embodiment of the invention.

FIG. 1 is a top view of a sensing device according to an embodiment of the invention.

Referring to FIG. 1, a sensing device 100 includes a base 102 and a response electrode 104, wherein the response electrode 104 and the base 102 are spaced apart from each other. The sensing device 100 is, for instance, a high electron mobility transistor (HEMT), a silicon-based field-effect transistor, a nanowire field-effect transistor, a carbon nanotube field-effect transistor, a graphene field-effect transistor, or a molybdenum disulfide field-effect transistor, but the invention is not limited thereto. In the present embodiment, the sensing device 100 is a transistor similar to a high electron mobility transistor.

The base 102 includes a substrate 108, a source end 110, a drain end 112, and a gate end 116 disposed between the source end 110 and the drain end 112. In the present embodiment, the method of forming the substrate 102 includes, for instance, forming a gallium nitride (GaN) layer and an aluminum gallium nitride (AlGaN) layer (not shown) on the substrate 108 in order and forming the source end 110, the drain end 112, and the gate end 116 on the substrate 108 via a lithography process.

The material of the substrate 108 is, for instance, silicon or sapphire. The low-dimensional heterostructure interface between the GaN layer and an aluminum indium nitride layer (not shown) can provide the base 102 with good carrier transport properties. In the present embodiment, the material formed on the GaN layer is aluminum indium nitride, but the invention is not limited thereto. In another embodiment, the material formed on the GaN layer can be other materials having piezoelectric properties, such as aluminum gallium nitride. The material of the source end 110 and the drain end 112 may include one or more than one conductive material. The conductive material is, for instance, a metal material, metal compound, or a combination thereof. The source end 110 and the drain end 112 are respectively connected to an external electronic device (not shown) via a circuit 136.

Referring further to FIG. 1, the response electrode 104 is disposed on the substrate 102. The response electrode 104 includes an electrode body 122 located on the top surface of the base 102, and the electrode body 122 is formed by a metal material. The response electrode 104 and the gate end 116 may be located on the same plane and the two may be spaced apart and disposed opposite to each other. More specifically, the electrode body 122 and the gate end 116 of the base 102 may be located on the same plane and the two may be spaced apart from each other and disposed opposite to each other, and the electrode body 122 and the base 102 are not electrically connected. Specifically, the electrode body 122 and the gate end 116 are not electrically connected. It should be mentioned that, the surface material of the electrode body 122 is selected from materials that can be bonded to a subsequently-selected acceptor. In the present embodiment, the surface material of the electrode body 122 is, for instance, gold.

Figure 2:
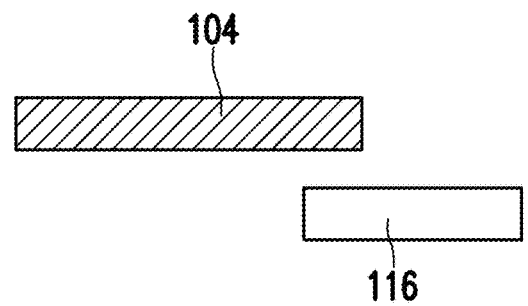
FIG. 2 is a cross section view of response electrode-gate end according to another embodiment of the invention.

FIG. 2 is a cross section view of response electrode-gate end according to another embodiment of the invention. In this embodiment, the response electrode 104 may be placed vertically above the gate end 116 of the base.

Figure 3:
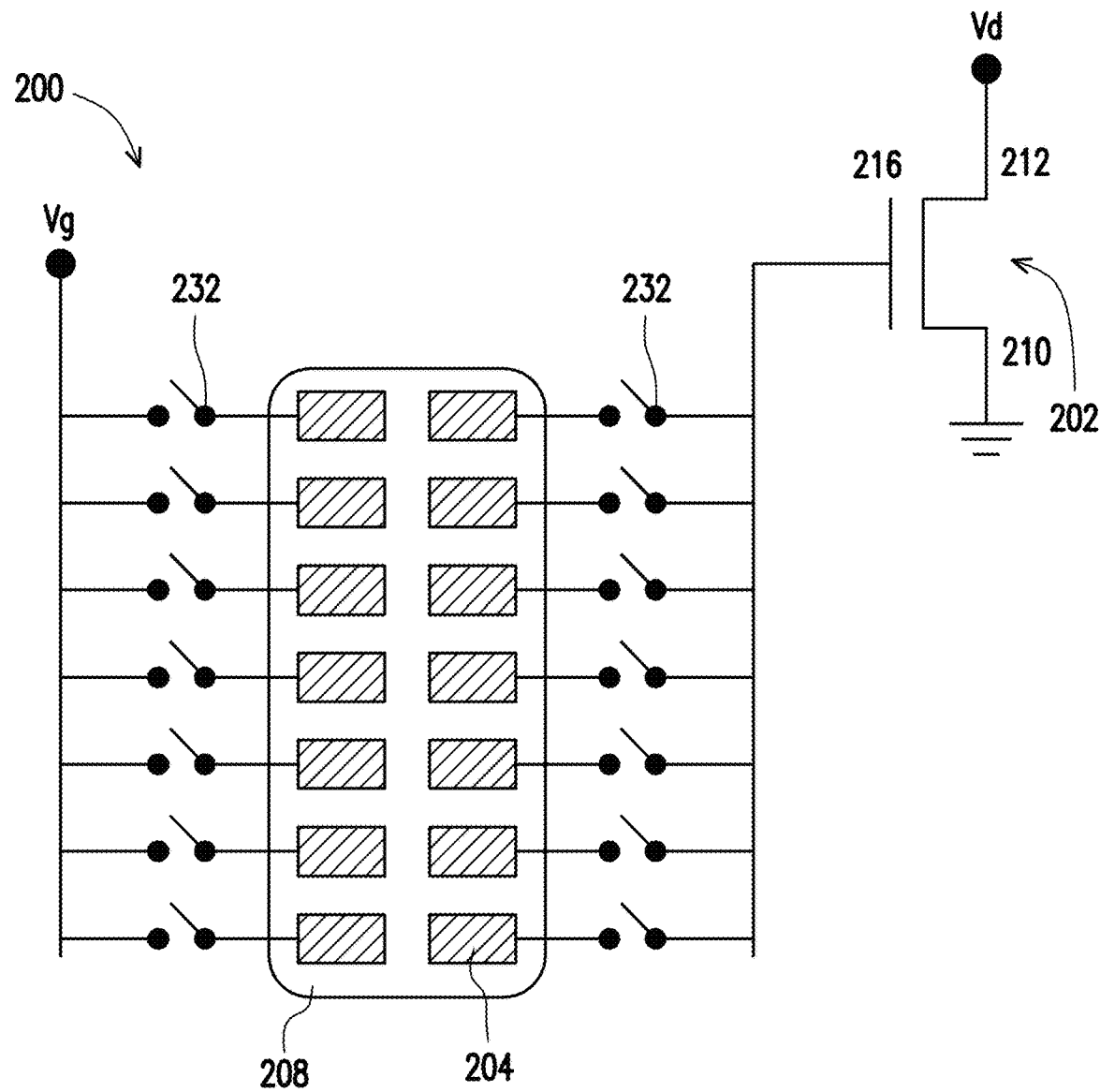
FIG. 3 is a top view of a sensing device according to another embodiment of the invention.

FIG. 3 is a top view of a sensing device according to another embodiment of the invention. A sensing device 200 shown in FIG. 3 is similar to the sensing device 100 shown in FIG. 1, and the difference is that the sensing device 200 has a plurality of response electrodes 204, and the plurality of response electrodes 204 are spaced apart on the substrate 208, and the same or similar components are described in detail above and are not repeated herein.

Referring to FIG. 3, the sensing device 200 includes a plurality of response electrodes 204, and the plurality of response electrodes 204 correspond to a same base 202.

Figure 4:
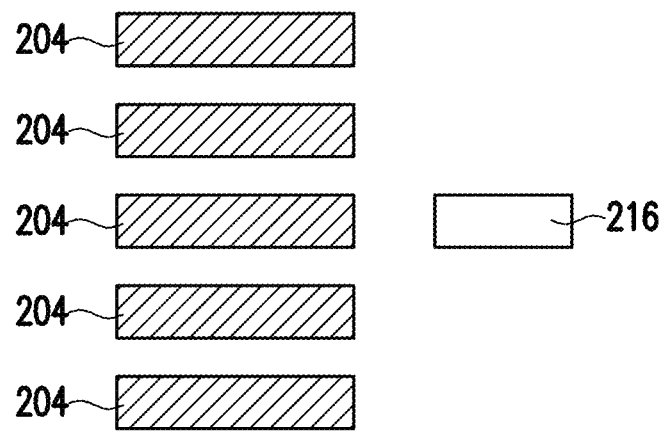
FIG. 4 is a top view of response electrode-gate end according to another embodiment of the invention.
Figure 5:
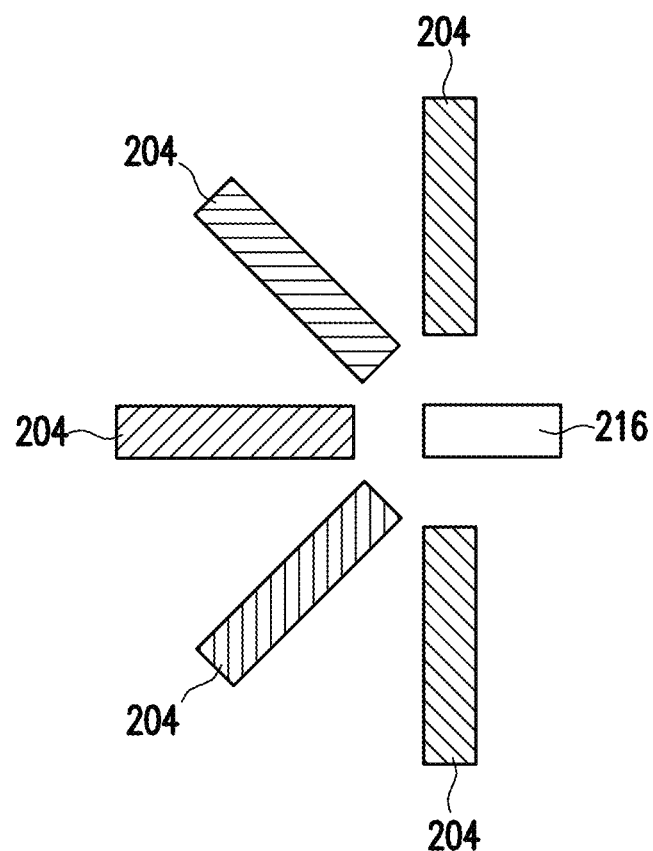
FIG. 5 is a top view of response electrode-gate end according to another embodiment of the invention.

FIG. 4 is a top view of response electrode-gate end according to another embodiment of the invention. In this embodiment, the plurality of response electrodes 204 are arranged in an array and used against the single gate end 216. FIG. 5 is a top view of response electrode-gate end according to another embodiment of the invention. In this embodiment, the plurality of response electrodes 204 are arranged radially and used against the single gate end 216. As a result, the sensing device 200 can perform a plurality of tests on analytes of the same or different types at the same time, which not only can increase the reliability of the test result, but can also reduce the time needed for the test. Moreover, since a plurality of response electrodes 204 share the same base 202 and only the used response electrode 204 needs to be changed to perform the next test, the cost for the test can be reduced.

In one embodiment, the sensing device 200 further includes a plurality of switch circuits 232 and each of the response electrodes 204 is connected to the corresponding switch circuit 232 to selectively control the desired response electrode 204, such that the sensing device 200 is suitable for various measurement methods, such as testing the same analyte at different times to observe the amount of change of concentration and time. In some embodiments, the switch circuit 232 is located at two opposite sides of the response electrode 204. The switch circuit 232 located at a side of the response electrode 204 is connected to a gate voltage Vg, and the switch circuit 232 located at another side of the response electrode 204 is connected to the gate end 216. Moreover, during the measurement, the source end 210 of the base 202 is grounded and a drain voltage Vd is applied to the drain end 212.

The invention also provides a blood detecting method using the sensing device above. Next, the blood detecting method of the invention is described via the sensing device 100 shown in FIG. 1.

First, a sensing device 100 is provided, wherein the sensing device 100 includes a base 102 and at least one response electrode 104, and the response electrode 104 is spaced apart from the base 102 relative to the gate end 116 of the base 102. In the present embodiment, the acceptor 106 may be bonded to the surface of the electrode body 122, wherein the acceptor 106 may be specifically bonded to the target to be tested. The acceptor 106 is, for instance, an antibody or an aptamer. In one embodiment, the sensing device may further comprise multiple types of acceptors disposed on a surface of the response electrode, and each type of acceptors can be specifically bonded to its corresponding type of target. More than one type of acceptor can be immobilized in the array of electrodes, to facilitate multiplexed biomarker detection. For example, in an array of 8 response electrodes, 8 different acceptors can be immobilized, to detect 8 different target biomarkers from single drop of blood.

Next, blood is placed on the response electrode 104, wherein the blood includes a plurality of blood cells and a plurality of targets. In the present embodiment, the blood is not pretreated (i.e., whole blood). In the present embodiment, the target is a disease biomarker. In one embodiment, the disease biomarker is, for instance, a cardiovascular disease biomarker, cancer biomarker, renal disease biomarker, or infectious disease biomarker. The cardiovascular disease biomarker is, for instance, a C-reactive protein (CRP), a brain natriuretic peptide (BNP), an N-terminal pro Brain natriuretic peptide (NT-proBNP), or a cardiac Troponin 1 (cTn1). In the present embodiment, the cardiovascular disease biomarker may be specifically bonded to the respective corresponding acceptor.

Next, the blood is separated into a first part and a second part, wherein the first part is in contact with the response electrode 104, and the blood cell count of the first part is less than the blood cell count of the second part. In the present embodiment, the method of separating the blood into the first part and the second part includes, for instance, inverting the sensing device 100 in which the blood is placed to separate the blood into the first part and the second part via gravity. Specifically, when inverting the sensing device 100, gravity causes the blood cells in the blood to stay away from the surface of the electrode body 122. In other words, the blood cells and plasma in the blood can be separated by gravity. In one embodiment, the first part of the blood is the plasma part and the second part is the blood cell part, and the response electrode 104 is only in direct contact with the plasma part containing a small amount of blood cells. In the present embodiment, the blood cells in the blood are kept away from the surface of the response electrode 104 using gravity by inverting the sensing device 100, but the invention is not limited thereto, and the blood cells in the blood may also be kept away from the surface of the response electrode 104 using other methods. Moreover, when the response electrode 104 is brought in contact with the first part, the target in the first part (plasma part) is specifically bound to the acceptor 106 bonded on the surface of the electrode body 122.

In the present embodiment, since the response electrode 104 is only in direct contact with the plasma part, interference to the blood cell part can be avoided during the detection of the target to obtain a more accurate test result.

Next, a voltage V is applied to the response electrode 104 such that an electric field F is generated between the response electrode 104 and the gate end 116 of the base 102, and a detection current I generated from the base 102 is measured to measure a property of the target (such as concentration). In some embodiments, the applied voltage may be a pulse voltage, a AC bias voltage, a DC bias voltage, or a voltage having multiple waveforms. Specifically, after a voltage is provided to the base 102, a voltage V is applied to the response electrode 104 to generate a voltage difference between the response electrode 104 and the gate end 116. Therefore, when the target is specifically bonded to the corresponding acceptor, a capacitance effect occurs between the response electrode 104 and the gate end 116 via the voltage difference generated by applying the voltage V to obtain a current value contributed by the capacitance effect. In the present embodiment, the electric field F is 0.1V/cm or more. In one embodiment, the electric field F is between 0.1 V/cm and 10 V/cm (0.1 V/cm≤F≤10 V/cm). In another embodiment, the electric field F is between 0.5 V/cm and 10 V/cm (0.5 V/cm≤F≤10 V/cm). In yet another embodiment, the electric field F is between 0.5 V/cm and 1.0 V/cm (0.5 V/cm≤F≤1.0 V/cm). The applied electric field F may have low detection limit and high sensitivity within the range above.

It should be mentioned that, when detection is performed using the capacitance effect, dynamic information of the acceptor and the target before the reaction reaches a balanced state can be measured. In other words, by measuring the dynamic information before the reaction reaches a balanced state, the shielding effect generated when human blood is balanced by high salt concentration as a result of measuring at balanced state can be overcome, and a complex dilution step is also not needed for the human blood.

In the present embodiment, the applied voltage may be a pulse voltage. The size of the pulse width and height of the pulse voltage can be adjusted according to the test duration and the size of the voltage needed for the test. In one embodiment, a time before the reaction of the acceptor and the cardiovascular disease biomarker reaches a balance is used for the pulse width, and the pulse width is not greater than $10^{-2}$ seconds, but the invention is not limited thereto. In an actual example, the pulse height is, for instance, 0.5 V, but the invention is not limited thereto.

In one embodiment, the applied voltage can be a single pulse (drain voltage=2 V, gate voltage=0.5 V, gate pulse width=0.5 μs) or a biphasic pulse (drain voltage=2 V, gate voltage=0.5 V, gate cycle pulse width=1 ms). In one embodiment, a pulse voltage can be continuously applied.

In the present embodiment, the measured detection current generated from a transistor can be optionally converted, such as integrally converting the detection current with respect to the pulse width. Current and time are integrated at this point, and the total amount of charges accumulated at the source end 110 of the base 102 at a specific time can be obtained.

In the present embodiment, the blood is separated into a plasma part and a blood cell part before a voltage is applied for testing, but the invention is not limited thereto. In another embodiment, the blood is separated into a plasma part and a blood cell part when the voltage is applied. In the present embodiment, since the response electrode is only in direct contact with the part containing a small amount of plasma, interference to the blood cell part is eliminated during the detection of the target, and therefore a more accurate test result can be obtained. Moreover, in the present embodiment, since a whole blood test can be directly performed without performing a pretreatment on the whole blood, cost and time of the whole blood test can also be reduced.

In the following, the blood detecting method and properties thereof provided by the invention are described in detail via experimental examples, but the following experimental examples are not intended to limit the invention. Moreover, the gain value in the experimental examples below represents the difference between a balance current value and an initial current value (i.e., background current) (i.e., balance current value-initial current value=gain value). The initial current value can represent the current value obtained by applying an initial voltage to the response electrode. In the present embodiment, the initial voltage can be less than the gate voltage, but the invention is not limited thereto. The balance current value can represent the current value obtained by applying a gate voltage Vg to the response electrode for a certain period of time.

Experimental Example 1

In experimental example 1, the sensing device 100 shown in FIG. 1 is used for the test. After human whole blood was added dropwise to the response electrode of the sensing device, the sensing device was inverted and current variation at different times was detected.

Comparative Example 1

A test was performed using a method substantially the same to that of experimental example 1, and the difference is only that human whole blood was added dropwise to the response electrode of the sensing device and then current values at different times were directly detected without inverting the sensing device.

Figure 6:
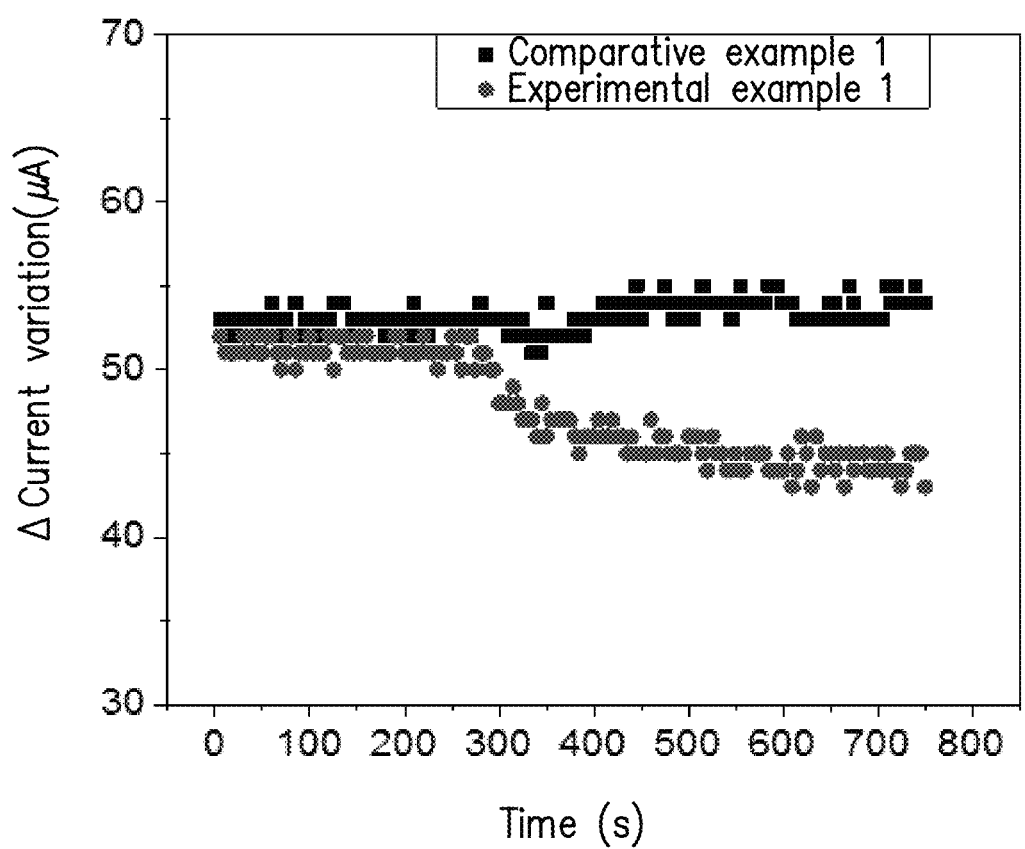
FIG. 6 shows the relationship between current variation and time of experimental example 1 and comparative example 1.

FIG. 6 shows the relationship between current variation and time of experimental example 1 and comparative example 1.

It can be seen from FIG. 6 that, the electrical signal is not changed with the increase in time during the testing of experimental example 1. On the other hand, in comparative example 1, after 4 minutes, the electrical signal is significantly reduced. It can be known from the results above that, since the sensing device is inverted during the test period of experimental example 1, gravity facilitates the separation of blood cells and plasma in the blood, and therefore the issue of interference from the blood cells can be alleviated. However, in comparative example 1, gravity causes precipitation of the blood cells, and once a large amount of blood cells approach the response electrode surface, the electrical signal is interfered.

To clearly describe the blood detecting method of the invention, 33 experimental examples are provided below.

It should be mentioned that, to ensure the acceptor is really bonded on the electrode body of the response electrode, before the measurement, the following measurement is performed first to confirm the acceptor is really bonded on the surface of the electrode body of the response electrode.

First, PBS (or human whole blood) was added dropwise on the response electrode and the base, and a buffer solution covers and is connected to the electrode body of the response electrode and the gate end of the base, and a pulse voltage having a pulse width and height of 50 μs and 0.5 V respectively was applied on the response electrode, and the source end of the base was measured to obtain a current value contributed by the PBS (or human whole blood). Next, the PBS (or human whole blood) was removed, and then the acceptor (antibody or aptamer) was added dropwise to the electrode body of the response electrode such that the acceptor is reacted and bonded to the electrode body of the response electrode. Next, PBS (or human whole blood) was added dropwise between the response electrode and the base, and the source end of the base was measured with a pulse voltage of the same conditions to obtain a current value contributed by the acceptor. When the current value contributed by the acceptor and the current value contributed by the PSB (or human whole blood) are different, the acceptor can be determined to be really bonded on the surface of the electrode body of the response electrode.

Experimental Example 2

In experimental example 2, the sensing device 200 shown in FIG. 3 was used for the test, wherein a specific aptamer of a C-reactive protein was bonded on the response electrode of the sensing device.

A reference protein solution containing 4% bovine serum albumin (BSA) was made via phosphate buffer saline (PBS), and the reference protein solution was added dropwise in the gap between the response electrode and the base, and the measurement conditions are as follows: Vd=2V, Vg=1 V, pulse time=100 μs. A first current I1 was measured at the drain end of the base.

Next, the bovine serum albumin solution between the response electrode and the base was washed away by an elution buffer. The reference protein solution containing 4% bovine serum albumin was used as a solvent, C-reactive protein was used as a solute, and a C-reactive protein solution having a concentration of 0.5 mg/L was made.

Next, the C-reactive protein solution was added dropwise on the response electrode, and measurement was performed with the same measurement conditions (Vd=2 V, Vg=1 V, pulse time=100 μs) to obtain a second current I2.

Lastly, the first current I1 was subtracted from the second current I2 to obtain a detection current I.

It should be mentioned that, in experimental example 1, the object of selecting a solution containing bovine serum albumin as the solvent is: since serum protein makes up the most protein in the blood, the ligand liquid is closer to the actual human blood environment, and the first current I1 was measured by adding a reference protein solution dropwise beforehand as a background value, and therefore by subtracting the first current I1 generated by the reference protein (BSA) from the second current I2 contributed by a C-reactive protein solution, the detection current I contributed by the combination of only the C-reactive protein and the acceptor can be obtained.

Experimental Example 3 to Experimental Example 6

Measurement was performed with substantially the same method as experimental example 2, and the difference is only in that the concentrations of the C-reactive protein solutions made in experimental example 3 to experimental example 6 were respectively 1.0 mg/L, 3.0 mg/L, 5.0 mg/L, and 10.0 mg/L.

Figure 7:
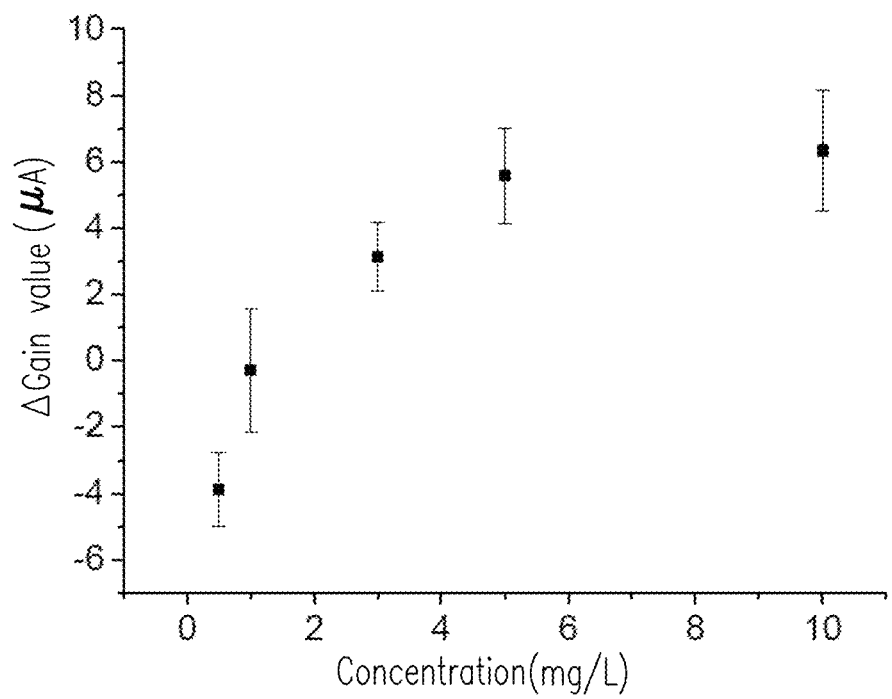
FIG. 7 shows the relationship between Δ gain value and concentration of experimental example 2 to experimental example 6.

FIG. 7 shows the relationship between Δ gain value and concentration of experimental example 2 to experimental example 6. It can be known from FIG. 7 that, Δ gain value is increased with increased concentration of C-reactive protein and a significant correlation is observed.

Experimental Example 7

Measurement was performed with substantially the same method as experimental example 1, and the difference is only in that a specific monoclonal antibody of cardiac Troponin 1 (cTn1) was bonded on the response electrode of the sensing device of example 7. Moreover, in example 7, a reference protein solution containing 4% bovine serum albumin was used as the solvent and cTn1 was used as the solute, and a cTn solution having a concentration of 0.024 ng/mL was made for measurement.

Experimental Example 8 to Experimental Example 10

Measurement was performed with substantially the same method as experimental example 7, and the difference is only in that the concentrations of the cTn solutions made in experimental example 8 to experimental 10 were respectively 0.24 ng/mL, 2.4 ng/mL, and 24 ng/mL.

Figure 8:
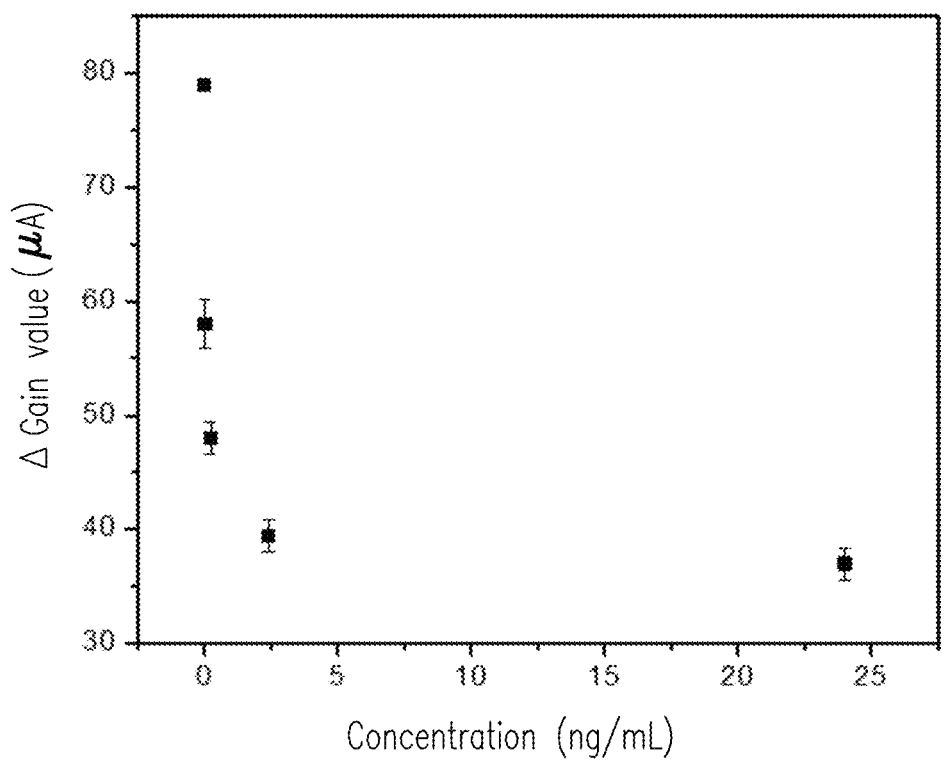
FIG. 8 shows the relationship between Δ gain value and concentration of experimental example 7 to experimental example 10.

FIG. 8 shows the relationship between Δ gain value and concentration of experimental example 7 to experimental example 10. It can be known from FIG. 8 that, Δ gain value is decreased with increased concentration of cTn1 and a significant correlation is observed.

Experimental Example 11

In experimental example 11, the sensing device 200 shown in FIG. 3 was used for the test, wherein a specific aptamer of a C-reactive protein was bonded on the response electrode of the sensing device.

Human whole blood was added dropwise in the gap the response electrode and the base, the sensing device was inverted, and the measurement conditions are as follows: Vd=2V, Vg=1 V, pulse time=100 μs. A first current I1 was measured at the drain end of the base.

Next, the human whole blood between the response electrode and the base was washed away by an elution buffer. Human whole blood was used as the solvent, C-reactive protein was used as the solute, and a C-reactive protein solution having a concentration of 1.28 mg/L was made.

Next, the C-reactive protein solution was added dropwise on the response electrode, the sensing device was inverted, and measurement was performed with the same measurement conditions (Vd=2 V, Vg=1 V, pulse time=100 μs) to obtain a second current I2.

Lastly, the first current I1 was subtracted from the second current I2 to obtain a detection current I.

Experimental Example 12 to Experimental Example 15

Measurement was performed with substantially the same method as experimental example 2, and the difference is only in that the concentrations of the C-reactive protein solutions made in experimental example 12 to experimental example 15 were respectively 3.26 mg/L, 4.26 mg/L, 5.26 mg/L, and 11.26 mg/L.

Figure 9:
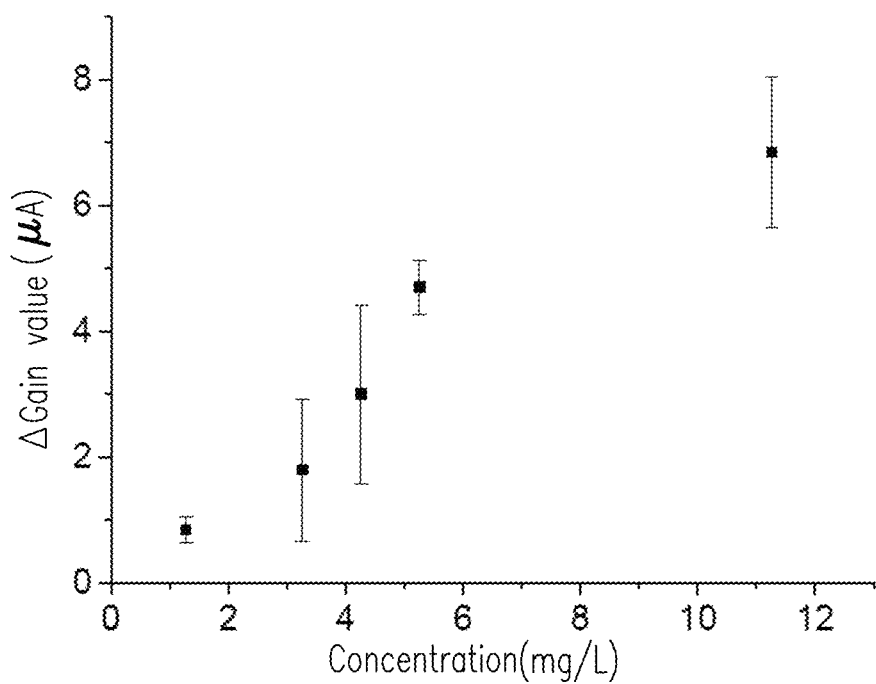
FIG. 9 shows the relationship between Δ gain value and concentration of experimental example 11 to experimental example 15.

FIG. 9 shows the relationship between Δ gain value and concentration of experimental example 11 to experimental example 15. It can be known from FIG. 9 that, Δ gain value is increased with increased concentration of C-reactive protein and a significant correlation is observed.

Experimental Example 16

Measurement was performed with substantially the same method as experimental example 11, and the difference is only in that a specific aptamer of N-terminal pro Brain natriuretic peptide (NT-proBNP) was bonded on the response electrode of the sensing device of example 16. Moreover, in experimental example 16, human whole blood was used as the solvent, N-terminal pro Brain natriuretic peptide (NT-proBNP) was used as the solute, and an NT-proBNP solution having a concentration of 100 pg/mL was made.

Experimental Example 17 to Experimental Example 19

Measurement was performed with substantially the same method as experimental example 16, and the difference is only in that the concentrations of the NT-proBNP solution made in experimental example 17 to experimental example 19 were respectively 450 pg/mL, 900 pg/mL, and 1800 pg/mL.

Figure 10:
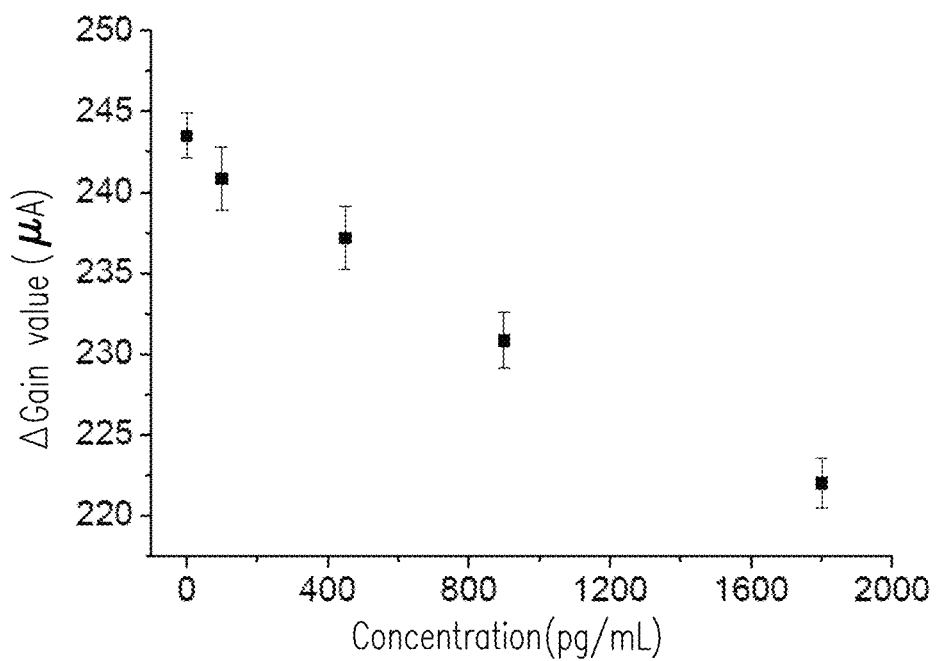
FIG. 10 shows the relationship between gain value and concentration of experimental example 16 to experimental example 19.

FIG. 10 shows the relationship between gain value and concentration of experimental example 16 to experimental example 19. It can be known from FIG. 10 that, the gain value is reduced with increased NT-proBNP concentration, and the correlation is significant.

Experimental Example 20

Measurement was performed with substantially the same method as experimental example 11, and the difference is only in that a specific aptamer of cardiac Troponin 1 (cTn1) was bonded on the response electrode of the sensing device of example 20. Moreover, in experimental example 16, human whole blood was used as the solvent, cTn1 was used as the solute, and a cTn1 solution having a concentration of 0.024 ng/mL was made.

Experimental Example 21 to Experimental Example 23

Measurement was performed with substantially the same method as experimental example 20, and the difference is only in that the concentrations of the cTnI solutions made in experimental example 21 to experimental 23 were respectively 0.24 ng/mL, 2.4 ng/mL and 24 ng/mL.

Figure 11:
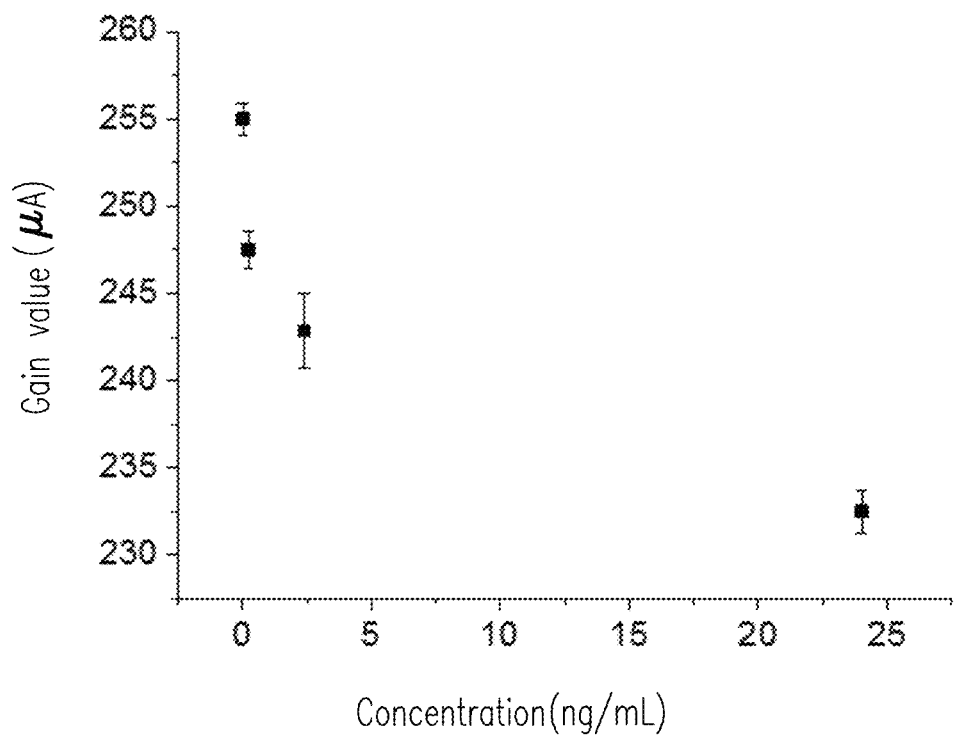
FIG. 11 shows the relationship between gain value and concentration of experimental example 20 to experimental example 22.

FIG. 11 shows the relationship between gain value and concentration of experimental example 20 to experimental example 23. It can be known from FIG. 11 that, gain value is decreased with increased concentration of cTn1 and a significant correlation is observed.

Experimental Example 24

Measurement was performed with substantially the same method as experimental example 11, and the difference is only in that a specific monoclonal antibody of C-reactive protein was bonded on the response electrode of the sensing device of example 24. Moreover, in example 24, human whole blood was used as the solvent, C-reactive protein was used as the solute, and a C-reactive protein solution having a concentration of 0.5 mg/L was made.

Experimental Example 25 to Experimental Example 27

Measurement was performed with substantially the same method as experimental example 24, and the difference is only in that the concentrations of the C-reactive protein solutions made in experimental example 25 to experimental example 27 were respectively 1.0 mg/L, 3.0 mg/L, and 10.0 mg/L.

Figure 12:
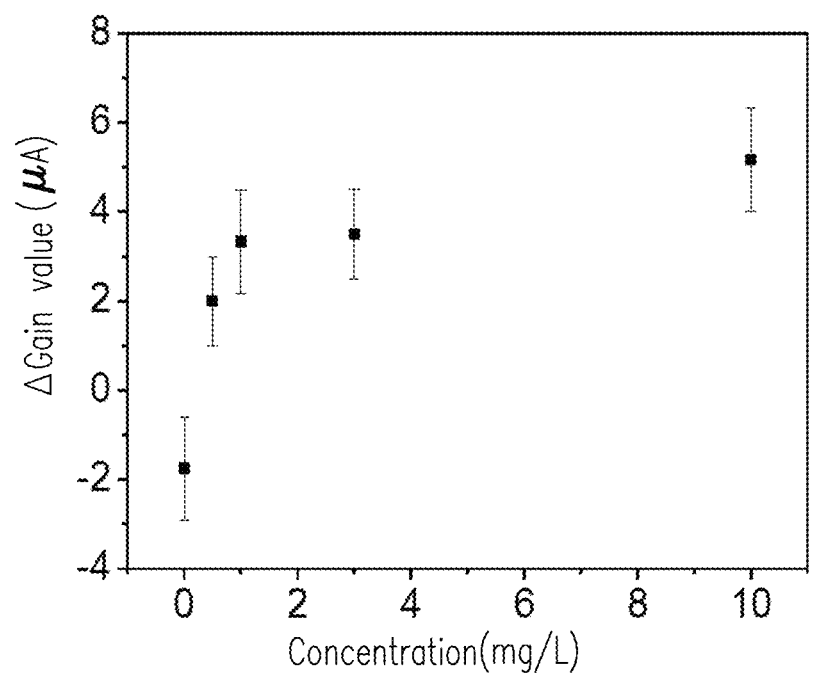
FIG. 12 shows the relationship between Δ gain value and concentration of experimental example 23 to experimental example 26.

FIG. 12 shows the relationship between Δ gain value and concentration of experimental example 24 to experimental example 27. It can be known from FIG. 12 that, Δ gain value is increased with increased concentration of C-reactive protein and a significant correlation is observed.

Experimental Example 28

Measurement was performed with substantially the same method as experimental example 11, and the difference is only in that a specific monoclonal antibody of brain natriuretic peptide (BNP) was bonded on the response electrode of the sensing device of example 28. Moreover, in example 28, human whole blood was used as the solvent, BNP was used as the solute, and a BNP solution having a concentration of 140 pg/mL was made.

Experimental Example 29 to Experimental Example 32

Measurement was performed with substantially the same method as experimental example 28, and the difference is only in that the concentrations of the BNP solutions made in experimental example 29 to experimental example 32 were respectively 644 pg/mL, 1570 pg/mL, 2980 pg/mL and 3900 pg/mL.

Figure 13:
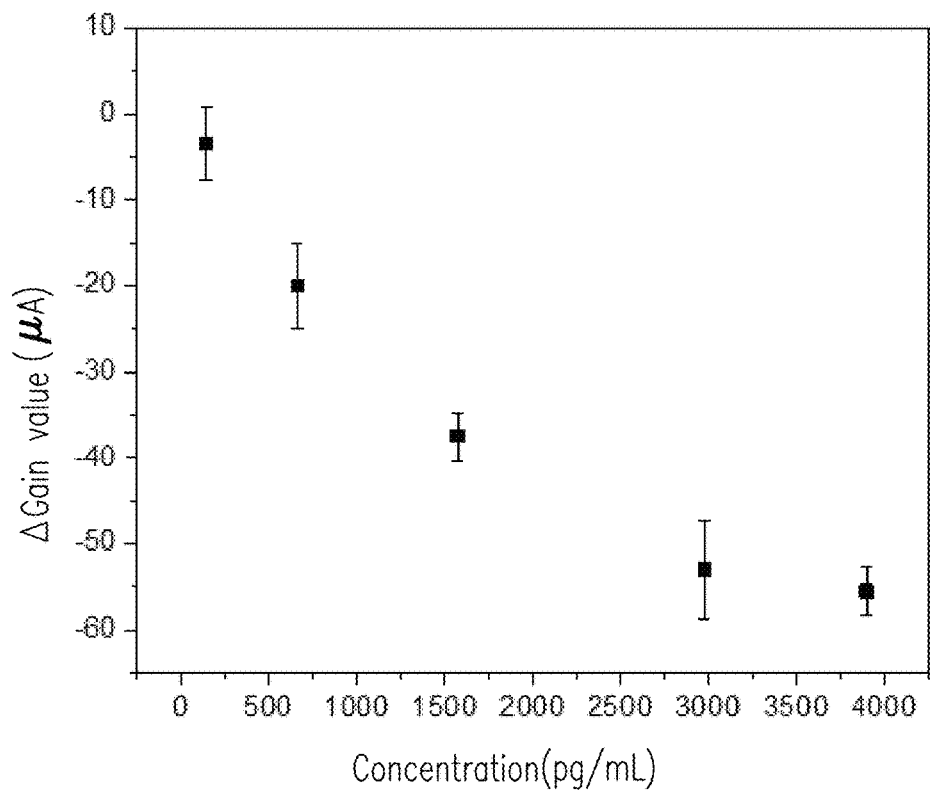
FIG. 13 shows the relationship between Δ gain value and concentration of experimental example 27 to experimental example 30.

FIG. 13 shows the relationship between Δ gain value and concentration of experimental example 28 to experimental example 32. It can be known from FIG. 13 that, Δ gain value is increased with increased concentration of BNP and a significant correlation is observed.

Experimental Example 33

Measurement was performed with substantially the same method as experimental example 11, and the difference is only in that a specific monoclonal antibody of cardiac Troponin 1 (cTn1) was bonded on the response electrode of the sensing device of example 33. Moreover, in example 33, human whole blood was used as the solvent, cTn1 was used as the solute, and a cTn solution having a concentration of 0.024 ng/mL was made.

Experimental Example 34 to Experimental Example 36

Measurement was performed with substantially the same method as experimental example 33, and the difference is only in that the concentrations of the cTn1 solutions made in experimental example 34 to experimental example 36 were respectively 0.24 ng/mL, 2.4 ng/mL, and 24 ng/mL.

Figure 14:
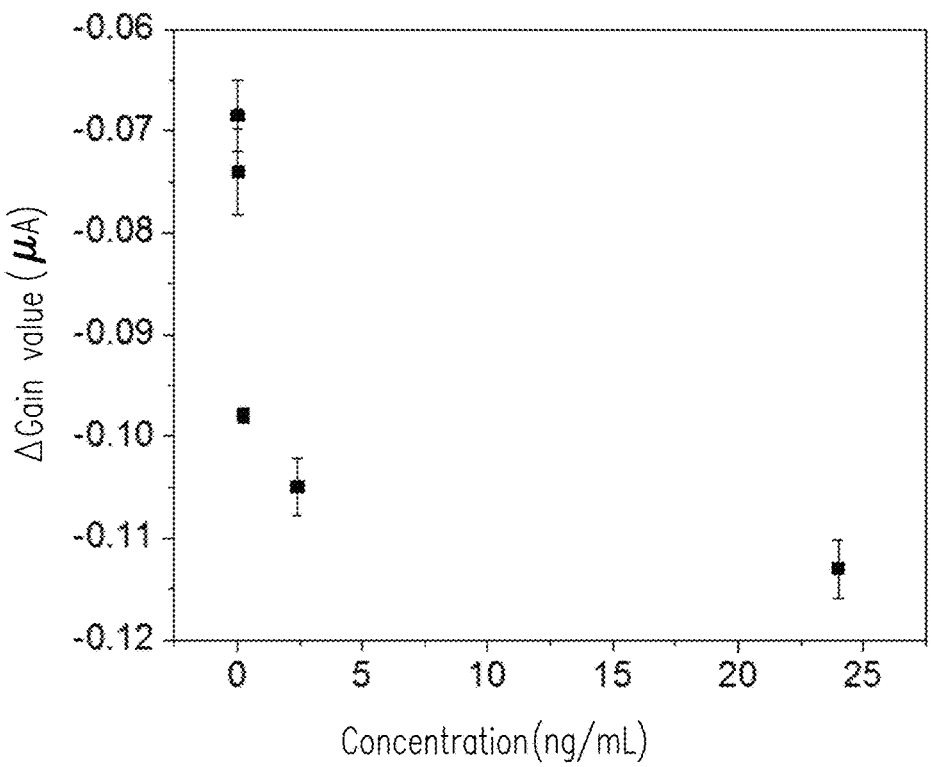
FIG. 14 shows the relationship between Δ gain value and concentration of experimental example 31 to experimental example 34.

FIG. 14 shows the relationship between Δ gain value and concentration of experimental example 33 to experimental example 36. It can be known from FIG. 14 that, Δ gain value is decreased with increased concentration of cTn1 and a significant correlation is observed.

Based on the above, the blood detecting method of the present embodiment can directly adopt whole blood for testing and interference to blood cells during testing can be reduced. Moreover, in the blood detecting method of the present embodiment, voltage difference is generated to the response electrode and the gate end spaced apart from each other and a capacitance effect is produced by applying a pulse voltage having an tunable pulse width and height to the response electrode to overcome a shielding effect and to directly test the target in the blood in high salt concentration. Moreover, the detecting method of the present embodiment has a gain effect, and therefore subtle electrical signal can be detected.

Although the invention has been described with reference to the above embodiments, it will be apparent to one of ordinary skill in the art that modifications to the described embodiments may be made without departing from the spirit of the invention. Accordingly, the scope of the invention is defined by the attached claims not by the above detailed descriptions.

What is claimed is:

1. A detecting method for blood, comprising:
providing a sensing device, wherein the sensing device comprises a base and at least one response electrode, and the response electrode is spaced apart from the base relative to a gate end of the base;
placing a blood on the response electrode, wherein the blood includes a plurality of blood cells and a plurality of targets;
separating the blood into a first part and a second part, wherein the first part of the blood is a plasma part and the second part is a blood cell part, and wherein the first part is in contact with the response electrode, and a blood cell count of the first part is less than a blood cell count of the second part; and
applying a voltage to the response electrode such that an electric field is generated between the response electrode and the gate end of the base and measuring a detection current generated from the base to measure a property of the target,
wherein a method of separating the blood into the first part and the second part comprises inverting the sensing device in which the blood is placed to separate the blood into the first part and the second part by a gravity.

2. The detecting method for blood of claim 1, wherein the electric field is F, and F is 0.1 V/cm or more.

3. The detecting method for blood of claim 1, wherein the target comprises a disease biomarker.

4. The detecting method for blood of claim 3, wherein the disease biomarker comprises a cardiovascular disease biomarker, a cancer biomarker, a renal disease biomarker, or an infectious disease biomarker.

5. The detecting method for blood of claim 1, wherein the sensing device further comprises an acceptor disposed on a surface of the response electrode, and the acceptor can be specifically bonded to the target.

6. The detecting method for blood of claim 1, the sensing device further comprises multiple types of acceptors disposed on a surface of the response electrode, and each type of acceptors can be specifically bonded to its corresponding type of target.

7. The detecting method for blood of claim 5, wherein the acceptor comprises an antibody or an aptamer.

8. The detecting method for blood of claim 6, wherein the acceptor comprises an antibody or an aptamer.

9. The detecting method for blood of claim 1, wherein the response electrode and the gate end of the base are located on a same plane.

10. The detecting method for blood of claim 1, the response electrode is separately disposed above the gate end of the base.

11. The detecting method for blood of claim 1, wherein the sensing device comprises a high electron mobility transistor, a silicon-based field-effect transistor, a nanowire field-effect transistor, a carbon nanotube field-effect transistor, a graphene field-effect transistor, or a molybdenum disulfide field-effect transistor.

12. The detecting method for blood of claim 1, wherein the sensing device comprises a plurality of response electrodes, and the plurality of response electrodes are spaced apart from one another.

13. The detecting method for blood of claim 12, wherein the sensing device further comprises a plurality of switch circuits, and each of the response electrodes is connected to a corresponding switch circuit.

14. The detecting method for blood of claim 12, the plurality of response electrodes are arranged in an array and used against the single gate end.

15. The detecting method for blood of claim 12, the plurality of response electrodes are arranged radially and used against he single gate end.

* * * * *